United States Patent [19]

Elefteriades

[11] Patent Number: 4,787,391
[45] Date of Patent: Nov. 29, 1988

[54] ANASTOMOTIC MARKING DEVICE AND RELATED METHOD

[76] Inventor: John A. Elefteriades, 503 Emerson Dr., Branford, Conn. 06405

[21] Appl. No.: 85,249

[22] Filed: Aug. 11, 1987

Related U.S. Application Data

[63] Continuation of Ser. No. 745,667, Jun. 17, 1985, abandoned.

[51] Int. Cl.$^4$ .......................... A61B 6/00; A61B 17/11
[52] U.S. Cl. .................................. 128/654; 128/325; 128/335.5; 128/334 R
[58] Field of Search .................... 128/653–654, 128/334 R, 335.5, 325, 1 R; 604/8; 623/1

[56] References Cited

U.S. PATENT DOCUMENTS

| | | | |
|---|---|---|---|
| 2,428,918 | 10/1947 | Miller | 128/334 R |
| 3,254,651 | 6/1966 | Collito | 128/334 R |
| 3,272,204 | 9/1966 | Artandi et al. | 128/334 R |
| 3,302,634 | 2/1967 | Mazellan | 128/654 X |
| 3,587,586 | 6/1971 | Kronenthal | 128/334 R |
| 3,626,947 | 12/1971 | Sparks | 623/1 X |
| 3,713,441 | 1/1973 | Thomas | 604/8 |
| 3,875,928 | 4/1975 | Angelchik | 128/325 X |
| 4,041,931 | 8/1977 | Elliott et al. | 623/1 X |
| 4,182,339 | 1/1980 | Hardy, Jr. | 623/1 X |
| 4,188,953 | 2/1980 | Klieman et al. | 128/325 |
| 4,202,349 | 5/1980 | Jones | 623/1 X |
| 4,205,399 | 6/1980 | Shalaby et al. | 623/1 |
| 4,219,520 | 8/1980 | Kline | 623/1 X |
| 4,271,070 | 6/1981 | Miyata et al. | 128/325 X |
| 4,280,954 | 7/1981 | Yannas et al. | 128/335.5 X |
| 4,416,028 | 11/1983 | Eriksson et al. | 623/1 |
| 4,506,676 | 3/1985 | Duska | 128/653 |
| 4,551,132 | 11/1985 | Pasztor et al. | 128/325 X |
| 4,556,060 | 12/1985 | Perlin | 128/325 |
| 4,586,503 | 5/1986 | Kirsch et al. | 128/334 R |
| 4,595,007 | 6/1986 | Mericle | 128/334 R |
| 4,606,337 | 8/1986 | Zimmermann et al. | 128/325 X |

FOREIGN PATENT DOCUMENTS 0530490  9/1977  U.S.S.R. .............................. 128/654

Primary Examiner—Kyle L. Howell
Assistant Examiner—Angela D. Sykes
Attorney, Agent, or Firm—McCormick, Paulding & Huber

[57] ABSTRACT

A sutureless, anastomotic marking device for the fluoroscopic localization of a coronary graft. Radiopaque indicators are circumferentially arranged around a centrally located opening in an absorbable hemostatic sheet material so that the indicators surround the anastomosis and are held in position by the fibrous tissues of the body to provide a radiopaque guide during angiographic procedure.

7 Claims, 1 Drawing Sheet

ANASTOMOTIC MARKING DEVICE AND RELATED METHOD

This is a continuation of co-pending application Ser. No. 745,667 filed on June 17, 1985 now abandoned.

BACKGROUND OF THE INVENTION

The present invention relates generally to angiography and deals more particularly with marking devices used for the fluoroscopic localization of coronary grafts.

The coronary artery bypass operative technique wherein a vein or other suitable conductor is grafted between the ascending aorta and the coronary arteries has been increasingly used in the repair and treatment of diseased hearts and associated blood carrying vessels to bypass and/or remove blockages which produce angina. Although the bypass operative technique is generally successful in the treatment of blockages associated with heart vessels, it has been observed that the bypass grafts do not always remain open. Consequently, the patency of coronary bypass grafts must often be monitored and evaluated in post-bypass patients.

An angiographic procedure which permits the roentgenographic visualization of a blood vessel that has been injected with a radiopaque substance is generally utilized by a cardiologist and a cardiovascular surgeon to assess the condition of the blood vessel being evaluated. The angiographic procedure which generally requires the insertion of a catheter into the vascular system, generally entering through the arm or groin area, to locate the opening of a bypass graft for injection of a radiopaque dye is generally very time consuming and difficult because there are no standard locations for coronary grafts. Therefore, the cardiologist must feel via the catheter the entire inner surface area of the ascending aorta for the dimple or notch present at a graft orifice. The hit or miss procedure in locating the coronary grafts can have the result that a graft not located may be mistakenly concluded to be blocked rather than missed. The cardiologist may make several angiographic dye injections in repeated attempts to locate the missing graft. The repeated attempts to locate missing grafts can be life threatening to the patient because the repeated dye injections place further burdens on the heart and each injection is accompanied by additional radiation exposure. In addition, the repeated attempts to locate missing grafts expose the cardiologist and the staff performing the angiographic procedure to dangerous radiation as well.

It is desirable therefore to have a coronary graft marker to aid in the localization of a coronary graft during catherization, minimize the time required to perform the angiographic procedure and reduce exposure to radiation.

Coronary graft markers are applied during coronary bypass surgery and provide a radiographic guide to improve localization of the graft during catherization. There are a number of currently available coronary graft markers, however, these markers are not entirely satisfactory and have significant short comings.

One currently available coronary graft marker requires the suturing of a steel or similar material washer to the aorta next to the anastomosis. Since the washer may be located at any point next to the anastomosis and not around it, localization is only approximate and actual usefulness during the angiographic procedure is limited.

Another problem associated with the washer marker is the requirement of suturing to the aorta. Each stitch during the operative procedure requires additional time and increases the risk of bleeding from the aorta or disruption of the anastomosis.

A further problem associcated with the washer marker is that if the anastomosis requires further attention during the operative procedure, the washer may impede access to the suture line joining the vein to the aorta.

An additional problem associated with the washer marker is that the rigidity of the marker may cause it to impinge on the anastomosis.

Yet an additional problem associated with the washer marker is that if a reoperation is required the rigid washer may impair the dissection and clamping of the aorta.

Another currently available coronary graft marker which overcomes some of the limitations of the washer marker is a semi-rigid steel ring which is opened, placed around the anastomosis, closed and sutured in place to the aorta. Because the ring surrounds the anastomosis, the accuracy problem associated with the localization of a coronary graft is overcome. Although the steel ring coronary graft marker overcomes the localization problem, it is characterized by additional problems and limitations.

One major problem associated with the steel ring marker is that since the ring surrounds the anastomosis, it may impinge on the graft and impair patency.

Another problem associated with the steel ring marker is the requirement of suturing to the aorta. As with the washer marker, additional time is required during the operative procedure to suture the ring to the aorta and each stitch increases the risk of bleeding from the aorta or disruption of the anastomosis. Additionally, because the ring surrounds the anastomosis a number of sutures may be required to position and maintain the ring in place to keep it from impinging on the graft.

A further problem associated with the steel ring marker is that if the anastomosis requires further attention during the operative procedure, the ring may impede access to the suture line.

An additional problem associated with the steel ring marker is that if reoperation is required, the size and bulk of the ring can seriously impair the dissection and clamping of the ascending aorta.

A general aim of the invention is therefore to provide a coronary graft marker that permits the accurate localization of a coronary graft during catherization, with a further aim being to provide such a coronary graft marker that does not require suturing to the aorta thereby minimizing the risk of bleeding and disturbance to the anastomosis.

These general aims are achieved in accordance with the invention and as described in more detail hereinafter, by a sutureless, anastomotic coronary graft marking device having radiopaque indicators attached to an absorbable hemostatic material sheet so that the indicators encircle the grafted artery and become attached to and held in place by fibrous tissues of the body without impinging on or interfering with the anastomosis.

Other objects and advantages of the invention will be readily apparent from the following detailed description and from the accompanying drawings forming a part thereof.

SUMMARY OF THE INVENTION

In accordance with the present invention, a sutureless, anastomotic marking device for the fluoroscopic localization of a coronary graft includes a hemostatic material arranged to encircle an anastomosis. Radiopaque indicators of an inert substance such as, gold, are attached to and circumferentially arranged on the hemostatic material encircling the anastomosis. The invention further resides in the hemostatic material dissolving during the anastomosis healing period so that the indicators come into physical contact with the proximal anastomosis coronary graft area and are held in position by the fibrous tissues of the body whereby the indicators provide a radiographic guide to localize the anastomosis during an angiographic procedure.

BRIEF DESCRIPTION OF THE DRAWINGS

FIG. 1 is a top plan view of a sutureless, anastomotic marking device embodying the present invention.

DETAILED DESCRIPTION

Figure 2:
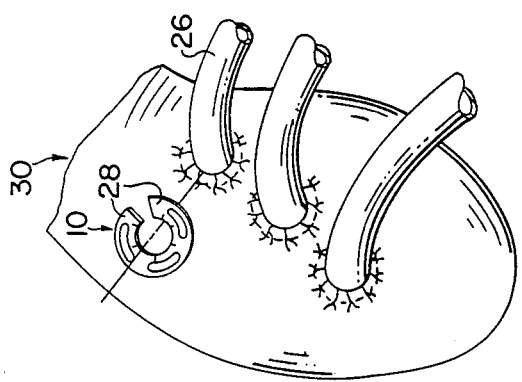
FIG. 2 is a perspective, somewhat schematic view of the marking device of FIG. 1 partially spread apart in preparation for placement around an anastomosis.

Considering now the invention in greater detail and referring to FIG. 1, a sutureless, anastomotic marking device embodying the present invention is shown schematically in a top plan view and is generally designated 10. The device 10 is made of a flexible, hemostatic sheet material suitable for use in the body and commonly referred to by the trade name "Surgicel", "Collastat" or other similar biological hemostatic material generally including collagen substances. The hemostatic material is however, preferably a microfibrillar collagen which has the characteristic of softening upon contact with body fluids and being completely absorbed or dissolved by the body over a period of time.

The hemostatic sheet of device 10 is preferably circularly arranged and having a donut shape with an outer edge 12, a centrally located opening 14 and an inner edge 16. The diameter of the opening 14 is made substantially equal to the diameter of a coronary artery bypass graft passing through it. A number of radial slits 18, 18 are cut through the hemostatic sheet material and extend radially outward from the inner edge 16 toward the outer edge 12 for some distance to form segments 20, 20 between the slits 18, 18. The segments 20, 20 move relative to one another to facilitate the encirclement of the device 10 around a bypass graft passing through the opening 14. One radial slit 22 extends completely from the inner edge 16 of the opening 14 to the outer edge 12 so that the device 10 may be spread apart for placement around the coronary artery bypass graft as described below.

Radiopaque indicators 24, 24 are made of a radiodense, inert material and each is attached to one surface of the hemostatic sheet by an adhesive which is suitable for use in the body and preferably is a silicon based adhesive and commonly referred to by the trade name "Silastic". The material of the radiopaque indicator 24 is preferably gold because it can be made into a very thin foil while retaining its radiopacity characteristic and because it is safe for permanent implantation in the body.

Figure 4:
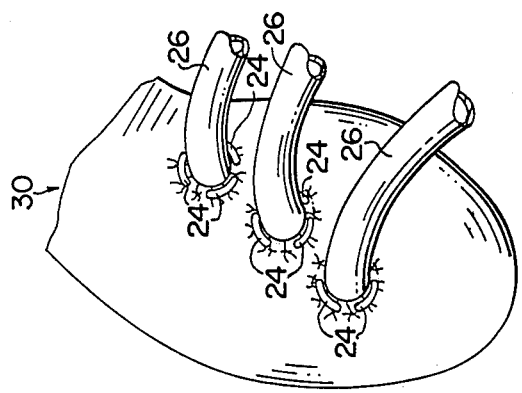
FIG. 4 illustrates somewhat schematically the radiopaque indicators encircling the proximal anastomoses to three coronary arteries after the hemostatic material of each marking device embodying the present invention has dissloved after placement around a respective anastomosis.
Figure 3:
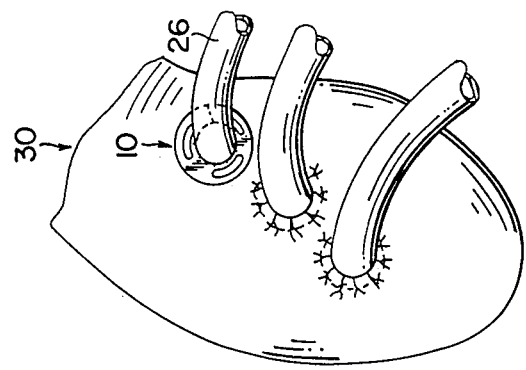
FIG. 3 is a somewhat schematic view of the marking device of FIG. 1 shown encircling an anastomosis.

Considering now FIGS. 2 through 4, FIG. 2 shows a marking device 10 partially opened along the cut radial slit 22 to form two half sections 28, 28 the half sections being on opposite sides of an axis extending between the outer edges 12, 12 of the device and along the slit 22. The two half sections are folded toward one another along the axis so that the indicators 24, 24 are generally facing one another and the half sections are in a plane substantially parallel to one another. The folded device is spread apart along the cut slit 22 and the device and artery bypass graft are moved relative to one another so that the artery bypass graft moves between the spread portions. The device is moved into enveloping relationship with the bypass graft artery so that the graft artery is situated between the half sections 28, 28 and extends through the central opening 14. The device is unfolded so that the two half sections 28, 28 lie generally in a common plane and surround the bypass graft artery passing through the central opening 14. The device is manipulated into a desired position and into contact with the anastomotic area.

As can be best viewed in FIG. 3, the marking device 10 is shown as it typically would be positioned after placement around a bypass graft artery 26 and in contact with an anastomotic area of the aorta generally designated 30. The hemostatic sheet material of the device 10 softens, as explained above, upon contact with body fluids and exhibits a characteristic stickiness to aid in maintaining the device in contact with the anastomosis without the need of suturing. If for any reason access to the anastomosis is required during the operation, the marking device 10 is simply lifted to expose the suture line.

The hemostatic sheet material will be absorbed or dissolved completely during the anastomosis healing period and the radiopaque indicators 24, 24 will have become fixed to the aortic adventitia by the fibrous tissues of the body and as illustrated in FIG. 4, the indicators encircle the coronary arteries 26, 26 and each associated anastomosis to provide a radiographic guide which is used to accurately locate the coronary graft during an angiographic procedure.

A sutureless, anastomotic marking device for the fluoroscopic localization of coronary grafts has been described in a preferred embodiment. It will be understood that numerous modifications and substitutions may be had without departing from the spirit of the invention. Therefore, the invention has been described by way of illustration rather than limitation.

I claim:

1. A sutureless, anastomotic marking device for the fluoroscopic localization of coronary grafts, said device comprising:

a sheet of flexible, hemostatic microfibrillar collagen, said hemostatic microfibrillar collagen being of the general type that dissolves after being in contact with body fluids for a period of time, said sheet having a first and second surface;

said sheet having an inner edge and defining a centrally located opening through the sheet for accommodating a coronary artery bypass graft passing therethrough, said opening having a diameter substantially equal to the diameter of said coronary artery bypass graft, said sheet further having an outer edge concentric with said central opening and defining an annular surface on said sheet first and second surface between said opening and said outer edge, said sheet having a plurality of means defining a slit extending radially outward for some distance from said opening in said sheet, said sheet having a number of said radial slits to facilitate the encirclement of said sheet around said bypass graft, and wherein one of said slits extends fully from said opening in said sheet to the outer edge of said sheet so that said sheet may be separated at said fully extended slit to allow the sheet to be placed about the bypass graft, a number of radiopaque indicators circumferentially arranged on one of said first and second surfaces, each of said indicators having a surface area substantially less than the annular surface area of said sheet, and means for attaching said radiopaque indicators to said one surface of said hemostatic sheet.

2. A sutureless, anastomotic marking device as defined in claim 1 further characterized by said radiopaque indicators being an inert material.

3. A sutureless, anastomotic marking device as defined in claim 2 further characterized in that said inert material is gold.

4. A sutureless, anastomotic marking device as defined in claim 1 further characterized in that said means for attaching is an adhesive substance.

5. A sutureless, anastomotic marking device as defined in claim 4 further characterized in that said adhesive substance is a silicon based adhesive.

6. A method of mounting an anastomotic marking device around a coronary bypass graft artery comprising the steps of:

providing a sheet of flexible, hemostatic material of the general type that dissolves after contact with body fluids for a period of time, said sheet further defining a centrally located opening therethrough;

arranging circumferentially around the opening a number of radiopaque indicators;

attaching the indicators to one surface of the hemostatic sheet;

cutting the hemostatic sheet from an edge of the central opening to the outer edge of the sheet so that the hemostatic sheet is separated completely along the cut part;

folding the sheet in on itself so that said indicators are generally facing one another and along a line extending along the cut part so as to form two half sections, each of said half sections being in a plane substantially parallel to one another;

spreading portions of the folded sheet along the cut part;

moving the bypass graft artery and the sheet relative to one another so that the graft artery moves between the spread portions of the sheet and the sheet moves into enveloping relationship with the graft artery and the graft artery is situated between the half sections and extends through the central opening;

unfolding the sheet so that the two half sections lie generally in a common plane and surround the graft artery extending through the central opening, said indicators being on the one surface away from the anastomosis and the other surface being in contact with the anastomotic graft area, and dissolving the hemostatic material during the anastomosis healing period so that the radiopaque indicators carried by the hemostatic material come into contact with the proximal anastomotic area of the coronary graft whereby the radiopaque indicators are held in contact with the anastomotic area by the fibrous body tissues surrounding the anastomosis.

7. A method of mounting an anastomotic marking device around a coronary bypass graft artery comprising the steps of:

providing a sheet of flexible, hemostatic material of the general type that dissolves after contact with body fluids for a period of time, said sheet further defining a centrally located opening therethrough;

arranging circumferentially around the opening a number of radiopaque indicators;

attaching the indicators to one surface of the hemostatic sheet;

cutting the hemostatic sheet from an edge of the central opening to the outer edge of the sheet so that the hemostatic sheet is separated completely along the cut part;

folding the sheet in on itself so that said indicators are generally facing one another and along a line extending along the cut part so as to form two half sections, each of said half sections being in a plane substantially parallel to one another;

spreading portions of the folded sheet along the cut part;

moving the bypass graft artery and the sheet relative to one another so that graft artery moves between the spread portions of the sheet and the sheet moves into enveloping relationship with the graft artery and the graft artery is situated between the half sections and extends through the central opening;

unfolding the sheet so that the two half sections lie generally in a common plane and in surrounding relationship to the graft artery extending through the central opening, said indicators being on the one surface away from the anastomosis and the other surface being in contact with the anastomotic graft area, and leaving the hemostatic sheet in surrounding relationship to the graft artery extending through the central opening to permit the hemostatic sheet to be dissolved by contact with body fluids during the anastomotic healing period so that the radiopaque indicators carried by the hemostatic material come into contact with the proximal anastomotic area of the coronary graft whereby the radiopaque indicators are held in contact with the anastomotic area by the fibrous body tissues surrounding the anastomosis.

* * * * *